United States Patent [19]

Lensmeyer

[11] Patent Number: 5,308,768
[45] Date of Patent: May 3, 1994

[54] SERUM WITH REDUCED LEVELS OF STEROIDS

[75] Inventor: Gary L. Lensmeyer, Fitchburg, Wis.

[73] Assignee: Wisconsin Alumni Research Foundation, Madison, Wis.

[21] Appl. No.: 46,681

[22] Filed: Apr. 13, 1993

[51] Int. Cl.$^5$ .................... G01N 33/78; G01N 33/96
[52] U.S. Cl. ....................................... 436/16; 436/17; 436/18; 436/817
[58] Field of Search ................ 436/8, 16, 17, 18, 817; 252/408.1

[56] References Cited

U.S. PATENT DOCUMENTS

| | | | |
|---|---|---|---|
| 4,404,285 | 9/1983 | Hou | 436/16 |
| 4,433,056 | 2/1984 | Baranczuk | 436/8 |
| 4,784,960 | 11/1988 | Baranczuk | 436/8 |

OTHER PUBLICATIONS

Textbook of Medicine, 19th Ed. Cecil, Ed. Wyngaard, Smith, Bennett, copyright 1992, pp. 1271–1272.
"Evaluation of SeraSub TM . . . For Making Calibrators and Controls for Drugs of Abuse", Clin. Chem. 37(6) 1991, Akerka.
"Evaluation of SeraSub TM a substitute . . . for making calibrators and controls", Alan P. Schwartz, Clin Chem 36(6) 1025, Jul. 1990.
Poster presented Jul., 1992 "Determination of cortisol (c), cortisone (cn), corticosterone (cc), prednisone (p), and prednisolone (pl) in serum with solid reversed-phase extraction and high performance liquid chromatography (HPLC)". Gary L. Lensmeyer, et al., Clin. Labs., (Univ. Wisc. Hosp. & Clinics, Dept. Path. & Lab. Med., Madison, Wis.).
Frey, et al., "Liquid-Chromatography Measurement of Endogenous and Exogenous Glucocorticoids in Plasma", Clinical Chemistry, vol. 25, No. 11:1944–1947, 1979.
McBride, et al., "Rapid Liquid-Chromatographic Method for Simultaneous Determination of Plasma Prednisone, Prednisolone, and Cortisol in Pediatric Renal-Transplant Recipients", Clinical Chemistry, vol. 37, No. 5:643–646, 1991.
Soldin, et al., "Development of a Radioreceptor Assay to Measure Glucocorticoids", Therapeutic Drug Monitoring, 14:164–168, 1992.
William Vine, Letters to the Editor, "Comments on Proficiency Testing", Clinical Chemistry, vol. 38, No. 10, 1992.
Advertisement from Biomedical Products, Jul., 1992 "Scantibodies Laboratory, Steroid Free Human Serum in Two Forms".
Advertisement from Creative Scientific Technology, Inc., Jun., 1993, "SeraSub —Liquid, Protein-Free Serum Substitute For Use in Manufacturing Clinical Chemistry and Immunological Standards and Controls".

Primary Examiner—Lyle A. Alexander
Assistant Examiner—N. Bhat
Attorney, Agent, or Firm—Quarles & Brady

[57] ABSTRACT

A blood serum sample useful as a calibration baseline comprising a natural blood matrix is disclosed. This serum sample contains less than an HPLC-detectable amount of cortisol. Also disclosed is a serum sample containing less than HPLC-detectable amounts of cortisone and corticosterone and less than RIA-detectable amounts of testosterone, androstenedione, progesterone, DHEA sulfate and 17-OH progesterone. A method of preparing such a serum sample is also disclosed.

4 Claims, 2 Drawing Sheets

SERUM WITH REDUCED LEVELS OF STEROIDS

FIELD OF THE INVENTION

The present invention relates to methods designed to analyze blood for steroid concentration. Specifically, the field of the present invention is calibration reagents useful in such methods.

BACKGROUND

Analytical procedures are only as reliable as the materials used to calibrate the procedures. These materials may be a sample without the analyte of interest (a "base-line calibration sample") or with a known amount of the analyte.

Good laboratory practice dictates the use of calibration samples prepared in a matrix identical to the matrix of the sample to be tested. With few exceptions, test accuracy will be compromised when this approach is not followed because new variables have been introduced to the test. Test methods that use extraction and immunoassay techniques are particularly sensitive to matrix composition and require proper validation of test accuracy with a designated matrix.

The usual way of preparing a calibration blank for an assay involving an exogenous analyte (such as a drug) is to supplement drug-free serum or urine with known quantities of the drug. Unfortunately, this method is problematic when the analyte is a normal endogenous biological constituent. Cortisol, for example, is a steroid present in all human sera. Adding pure cortisol to native human sera will produce an inaccurate calibration blank. Because endogenous steroids are normal constituents of serum, they must be removed from a calibration serum sample before standard amounts of a steroid can be added.

To circumvent this problem, investigators and commercial manufacturers often prepare cortisol calibration blanks in dilute albumin solutions or in a serum matrix that has been significantly altered during the process of removing endogenous cortisol. For example, McBride et al., *Clinical Chem.*, 37[5], 1991, describes cortisol calibration blanks prepared in a dilute albumin solution, rather than in serum. Accordingly, when immunoassays are used to test for cortisol (or other steroids) accuracy problems can surface that are due, in part, to dissimilarity between the matrices of the calibration blank and the test specimen. Deviations from the usual sample environment will affect chemical interactions, analytical response, and overall accuracy. Discrepancies are most obvious when popular commercial immunoassays are evaluated against reference chromatographic/mass spectrometry methods.

Some investigators do not remove steroids but instead use a standard addition technique. With this technique a known quantity of a steroid standard is added to test sample. Both native test sample with and without added standard are analyzed. The difference between the two results represents the analytical response for the standard. The remaining response is from the steroid in the native test sample. This indirect method of standardizing is rarely used because of potential accuracy problems. (Frey, et al., *Clinincal Chem.* 25[11], 1979.)

A common method of removing steroids from serum is with charcoal. Soldin et al., *Therapeutic Drug Monitoring*, 14:164–168, 1992, describes charcoal adsorption of steroids. This treatment is a harsh process that will nonspecifically adsorb both steroids and other endogenous compounds. It is difficult to remove residual charcoal from serum, and even trace amounts can interfere in subsequent assays that use the steroid-stripped serum as a calibration base sample. Processes used to remove charcoal can introduce contaminants into serum.

What is needed in the art of analyte analysis is a serum sample useful as a calibration base-line comprising a natural blood serum matrix.

SUMMARY OF THE INVENTION

The present invention is a blood serum sample useful as a calibration base-line comprising a natural blood matrix. The serum sample contains less than 30 ng/mL cortisol. By "natural blood serum matrix" we mean that the natural blood serum chemistry has not been significantly disrupted by the removal of endogenous and exogenous steroids and exogenous drugs. In a preferred form of the present invention, the serum sample contains less than 5 ng/mL cortisol.

The present invention is also a serum sample containing less than 5 ng/mL cortisone, 5 ng/mL corticosterone, 0.1 ng/mL testosterone, 0.1 ng/mL androstenedione, 0.4 ng/mL progesterone, 5 mcg/dL dehydroepiandrosterone sulfate, and 0.4 ng/mL 17-OH progesterone.

The present invention is also the serum sample described above containing less than 10 ng/mL amitriptyline, 10 ng/mL nortriptyline, 10 ng/mL doxepin, 10 ng/mL desdoxepin, 10 ng/mL desipramin, 10 ng/mL imipramine, 10 ng/mL desipramine, 10 ng/mL amoxepine, and 10 ng/mL 8-OH amoxepine.

In a preferred form of the present invention, the serum sample contains less than 0.1 mcg/mL caffeine, 0.1 mcg/mL diazepam, and 0.1 mcg/mL nordiazepam.

The present invention is also a blood serum sample useful as a calibration base-line comprising a natural blood matrix wherein said serum sample contains an amount of cortisol less than that detectable by HPLC. The present invention is also a serum sample useful as a calibration base-line comprising a natural blood serum matrix containing less than HPLC-detectable amounts of cortisol, cortisone, and corticosterone and less than RIA-detectable amounts of testosterone, androstenedione, progesterone, dehydroepiandrosterone sulfate, and 17-OH progesterone.

In a preferred form of the present invention, the serum sample also contains less than HPLC-detectable amounts of amitriptyline, nortriptyline, doxepin, desdoxepin, desipramin, imipramine, desipramine, amoxepine, and 8-OH amoxepine.

In another preferred form of the present invention, the serum sample contains less than an GC-Ms (gas chromatography/mass spectrometry)-detectable amounts of caffeine, diazepam and nordiazepam.

In a preferred form of the invention, the serum sample is human blood.

The present invention is also a method of preparing a serum sample. This method comprises the steps of first obtaining a serum pool, wherein the serum contains endogenous steroids, and then removing the cryoprecipitates and insoluble material from the pool. The pool is applied to at least one solid-phase sorbent column where the steroids are retained on the column. The eluant is collected.

In a preferable form of the present invention, the pool is applied to at least two solid-phase sorbent columns and the solid-phase sorbent column is $C_{18}$ bonded silica.

In another preferable form of the present invention, cryoprecipitates and other insoluble material are removed by two freeze-thaw cycles.

It is an object of the present invention to provide a serum sample that contains natural blood constituents, but does not contain cortisol. This serum sample is useful as a calibration base-line in analytical procedures that measure cortisol.

Another object of the present invention is to provide a serum sample that contains natural blood constituents, but lacks cortisol, cortisone, crticosterone, testosterone, androstenedione, progesterone, dehydroepiandrosterone sulfate, and 17-OH progesterone. This blood serum sample is useful to provide a base-line calibration sample in analytical procedures designed to measure these steroids.

It is another object of the present invention to provide a serum sample useful for base-line calibration in assays to measure serum levels of anti-depressants and other drugs.

It is a feature of the present invention that the base-line calibration sample retains the constituents of the normal blood serum matrix.

It is another feature of the present invention that the base-line calibration sample retains the constituents of the normal human blood serum matrix.

It is another feature of the present invention that the serum sample is prepared without the use of charcoal.

Other objects, advantages, and features of the present invention will become apparent after review of the specification, drawings and claims.

DESCRIPTION OF THE INVENTION

The present invention is a calibration base-line sample comprising a blood serum sample with reduced levels of steroids. The present invention is also a procedure designed to obtain this serum sample. This calibration blank retains the essential chemical characteristics of serum, is a reliable serum base-line for analytical methods, and can be used to prepare accurate calibration samples for analytical methods.

Figure 1:
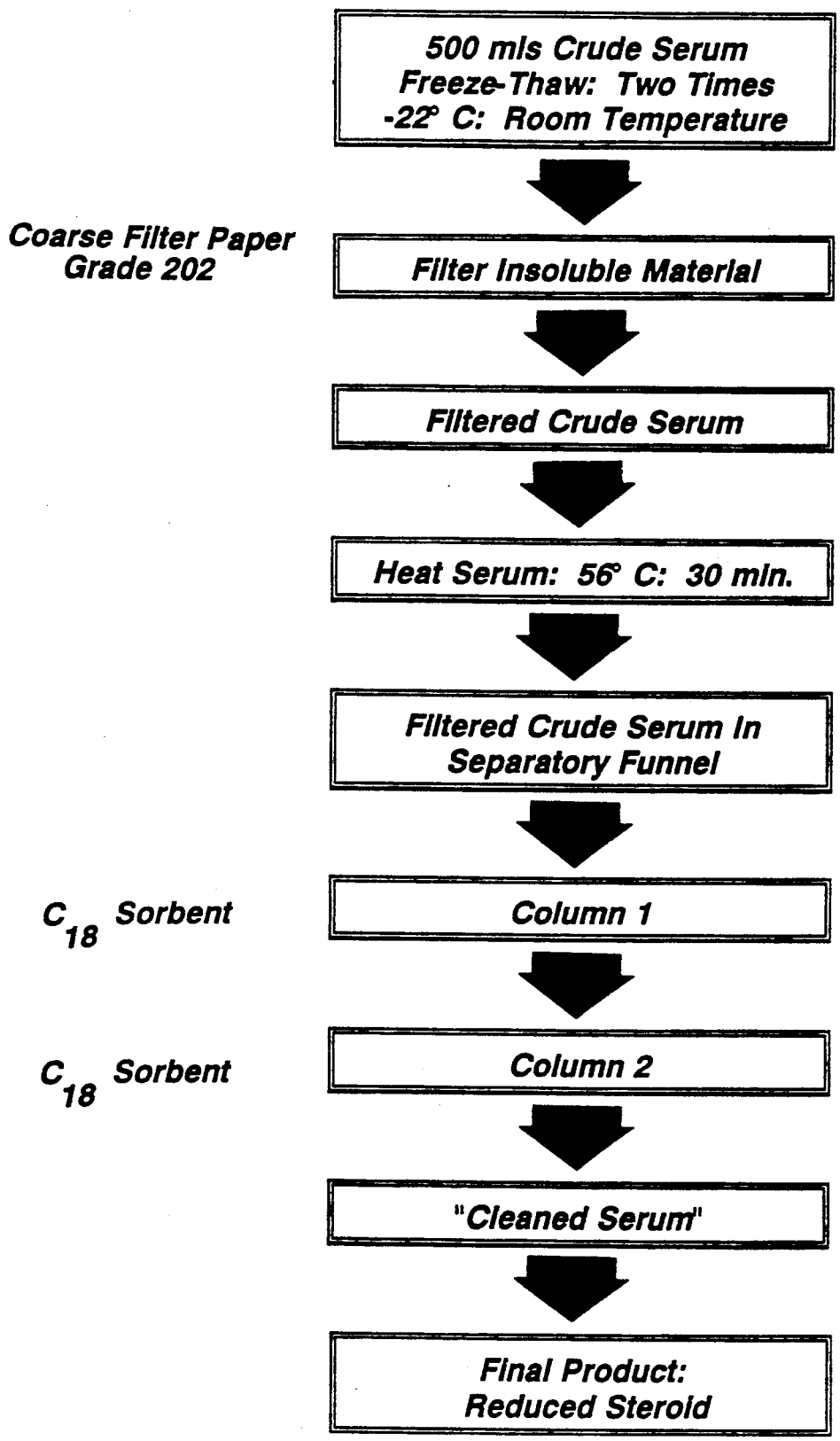
FIG. 1 is a schematic diagram of a preferred embodiment of the method of the present invention.
Figure 2:
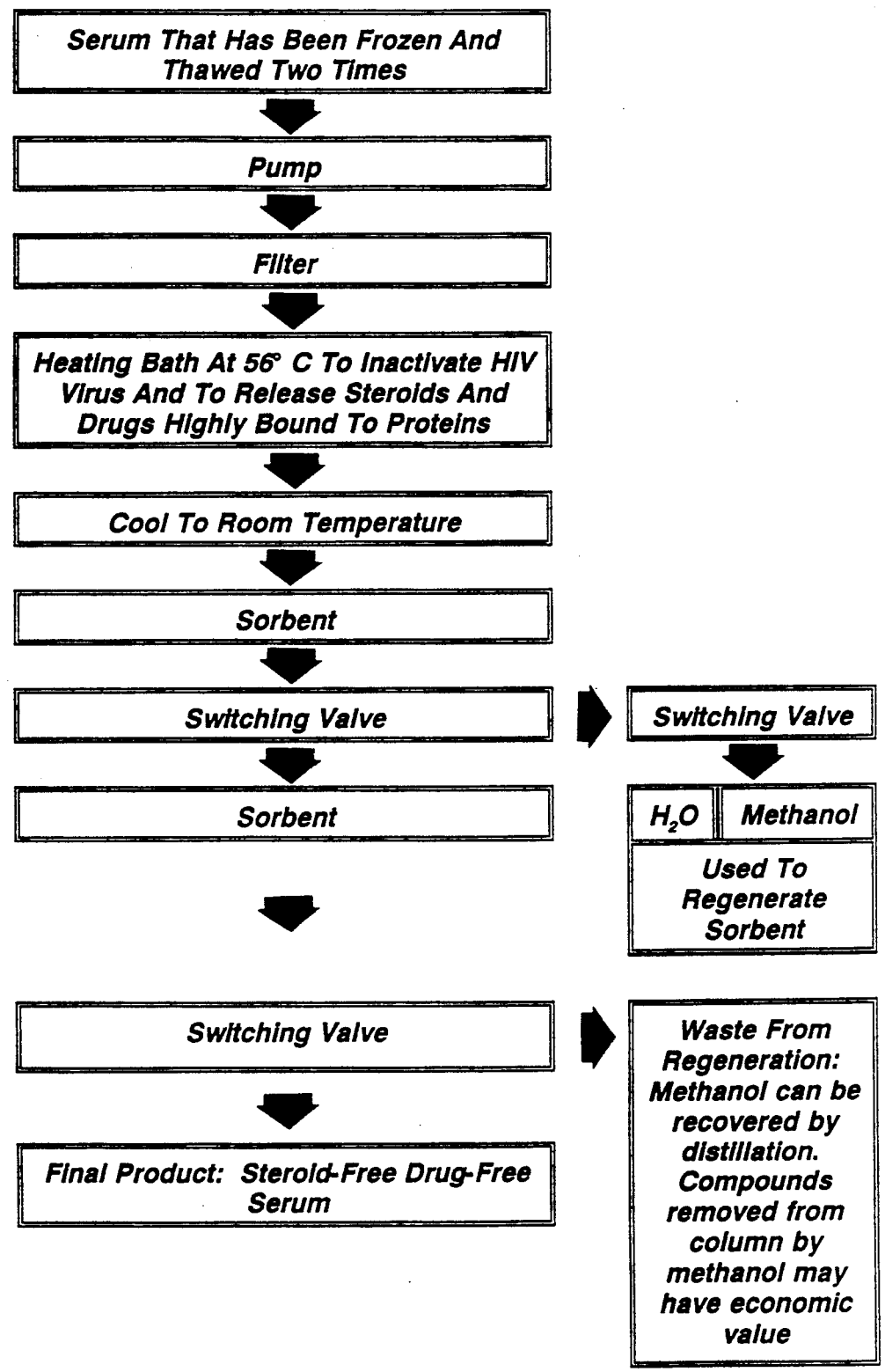
FIG. 2 is a schematic diagram of another embodiment of the present invention.

Briefly, the procedure consists of four steps: 1) preparation of a serum pool, 2) removal of cryoprecipitates and insoluble material, 3) release of steroids from proteins and inactivation of HIV virus, and 4) removal of steroids and drugs with a solid phase sorbent. FIG. 1 illustrates a preferred example of this procedure. A suitable "scaled-up" procedure is diagramed in FIG. 2. By "small scale" procedures, we mean an initial serum pool volume of less than 1-3 liters. By "large scale", we mean an initial serum pool volume of greater than 1-3 liters.

Steroids are commonly measured in serum by HPLC (high performance liquid chromatography) or RIA (radio immunoassay). In a preferred form of the invention, the serum sample contains less than an HPLC-detectable amount of cortisol, cortisone, and corticosterone, less than an RIA-detectable amount of testosterone, androstenedione, progesterone, 17-OH progesterone and DHEA sulfate. By "HPLC-detectable" or "RIA-detectable" we mean that an HPLC analysis or an RIA analysis, such as the ones we describe, detect none or a de minimus amount of the steroid or drug. The de minimus amount of drug or steroid depends on the test methodology used and is different for each steroid or drug. In each case he detection limit of the respective assay is the de minimus amount. (See Table 4 for this information.)

1. PREPARATION OF A SERUM POOL

Usual collection protocols are preferably used to obtain one unit volumes of blood from human volunteers. Preferably, the blood is collected in glass containers with no additives. Testing of individual blood units may be necessary to eliminate hepatitis-infected and AIDS-infected blood from the pool. A donor questionnaire would allow acquisition of information concerning drug medications, diseases, and time of last food intake. Even though the clean-up process will remove drugs from the serum, it is worthwhile to collect medication information, particularly as a quality control/trouble-shooting measure. Also, to minimize the dietary fat (chylomicrons) in serum, blood should be drawn at least two hours after food intake. These unit volumes are mixed together to form a pool.

2. REMOVAL OF CRYOPRECIPITATES

Removal of cryoprecipitates and insoluble material is preferably done by a freeze-thaw process. On a small scale, the pooled serum is frozen (preferably at $-22°$ C.) for one day and then thawed at room temperature. This freezing and thawing procedure is usually repeated a second time. After the two freeze-thaw procedures, particulate matter is removed from the serum pool. Preferably, this is done by passing the serum pool through a coarse filter paper, such as Whatman grade 202.

In a scaled-up procedure (FIG. 2) large containers holding pooled serum can be wheeled into walk-in freezers. To thaw the serum, these containers may be left at room temperature. Similar to a small scale procedure, this serum must filtered to remove particulate matter.

3. RELEASE OF STEROIDS FROM PROTEINS

In this step, the serum is heated to release steroids and drugs that are bound to proteins. This removal improves the efficiency of drug and steroid removal by the solid phase column. Additionally, the heating will inactivate the AIDS (HIV) virus. The heating temperature is critical because we do not want to denature proteins. The temperature and time for AIDS inactivation is an established, recommended procedure. (McDougal, et al, *J. Clin. Invest.*, 76:875-877, 1985)

In a small scale procedure, the serum pool is preferably equilibrated at 56° C. for thirty minutes. However, equilibration at a temperature range of 56° to 57° C. for 30 min. to 45 min. time would be sufficient.

In a large scale procedure (FIG. 2) the filtration step above is preferably performed in combination with the heating step and the application to the solid-phase column discussed below. These steps can be performed in a continuous flow process using a peristaltic pump to move serum through appropriate tubing. Note that the tubing or other apparatus contacting serum must not introduce contaminants into the serum. The serum can flow through a filter, into a heating bath, and onto the solid-phase column discussed below.

4. REMOVAL OF STEROIDS AND DRUGS

The serum is next applied to a solid-phase sorbent column. By "solid-phase sorbent" we mean a column material comprised of silica or polymeric-based particles chemically bonded with phenyl, alkyl or ionic ligands. Preferred solid phase sorbents are bonded silica or polymeric particles and ion exchange sorbents. Especially preferred solid phase sorbents are $C_8$ and $C_{18}$ bonded silica.

In a large scale application, the serum is applied through a small disposable sorbent guard cartridge that will retain irreversibly bound materials and protect the main sorbent column. The appropriate size of the guard and main sorbent columns can be determined empirically with capacity studies. Periodically, switching valves can be activated to regenerate the main column using methanol and water washes. This process will clean the sorbent of retained steroids and drugs. Methanol present in the waste can be recovered by distillation. Column regeneration and methanol distillation are cost-saving measures.

In a small scale procedure, two solid-phase sorbent columns, each preferably containing 60 grams of $C_{18}$ bonded silica are primed by passing through 50 mL methanol and then 50 mL water. The first column is supported on a ring stand and filled with the pooled serum which is allowed to pass through the column by gravity. The first 12 mLs of this eluant will represent column dead volume and be discarded.

The second $C_{18}$ column is placed underneath the first column in series such that the serum eluding from the first column passes directly into the second column. Again, the first 12 mL of eluant is discarded. All subsequent serum is collected and saved.

To regulate the filling of the first column with filtered unprocessed serum, a 500 mL separatory funnel is positioned above the columns and the flow is regulated with a stopcock.

The final product is stored frozen ($-22°$ C.) or refrigerated ($4°$ C.) in sterile glass bottles or tubes. Preferably, the product should not be lyophilized. Lipids do not solubilize adequately when lyophilized serum products are reconstituted with water.

5. USE OF BASE-LINE SERUM SAMPLE IN ASSAY

The serum sample of the present invention is used to prepare baseline and standard calibration solutions for use in commercial tests, such as immunochemical test systems, that test serum for the steroids cortisol, cortisone, corticosterone, androstenedione, dehydroepiandrosterone sulfate, testosterone, progesterone, and 17-OH progesterone. Preliminary work in our laboratory suggests that other steroids (11-deoxycortisol, deoxycorticosterone, prednisone, prednisolone, and methylprednisolone) are also removed from serum in the process disclosed above. Accordingly, manufacturers of commercial test systems for these steroids and selected drugs can use the serum product to improve existing procedures and to develop other procedures.

The serum product is also used to prepare baseline and standard calibration solutions by individual laboratories that develop their own analytical test procedures for the above-mentioned steroids and drugs. Poor quality, high cost, or unavailability of commercial test systems are some reasons "in-house" test procedures are developed.

Proficiency testing agencies that require licensed laboratories to get passing grades on challenge test samples would benefit from the serum product. Unfortunately, these agencies have a history of supplying test specimens with a matrix dissimilar to the matrix of specimens routinely tested by the participating laboratories. The serum sample of the present invention is more representative of the "real world" specimen and would be a better tool to evaluate selected steroid and drug testing methodologies.

6. NON-HUMAN SERUM

This process could be extended to processing serum from a variety of animal species, thereby meeting a need in veterinary medicine testing. One would modify the procedure by using animal serum to prepare the baseline sample.

EXAMPLES

1. Preparation Of Serum With Reduced Levels Of Steroids And Drugs

FIG. 1 describes a preferred method of the present invention. Ten 10-mL tubes of blood were collected per person from 15 individuals. Blood was collected in additive-free glass tubes from volunteer donors. Volunteers were healthy males and females 25–40 years old employed at the University of Wisconsin.

Serum was separated from cells by a standard centrifugation procedure and the sera from all donors was pooled.

The pooled serum (500 mLs) was frozen ($-22°$ C.) for one day and then thawed at room temperature. The freezing and thawing procedure was repeated a second time. This process removed cryoprecipitates and other particulate material that would otherwise come out of solution when the final product is frozen and then thawed.

The serum pool was then passed through coarse filter paper (Whatman grade 202) to remove particulate matter.

The cold serum pool was equilibrated at $56°$ C. for 30 min. This heating released steroids and drugs from bound proteins, thereby improving the efficiency of drug and steroid clean-up by the sorbent column. Additionally, the heating inactivates the AIDS (HIV) virus.

Two solid phase sorbent columns, each containing 60 grams of $C_{18}$ bonded silica, were primed by passing through 50 mL methanol and then 50 mL water. The $C_{18}$ column was obtained from Varian Sample Preparation Products, Harbor City, Calif. The first column was supported on a ring stand and filled with the pooled serum, which was allowed to pass through the column by gravity. The first 12 mLs of eluate represented column dead volume and was discarded.

The second $C_{18}$ column was placed underneath the first column in series such that serum eluting from the first column passed directly into the second column. The first 12 mLs of eluate that passed from the second column was discarded. All subsequent serum was collected and saved. To regulate filling of the first column with filtered unprocessed serum, a 500 mL separatory funnel was positioned above the columns and the flow was regulated with the stopcock.

The final product was stored frozen ($-22°$ C.) or refrigerated ($4°$ C.) in sterile glass bottles or tubes. Preferably, the product should not be lyophilized.

2. BIOCHEMICAL PROFILE OF SERUM

The constituents of the serum with reduced levels of steroids and drugs are essentially identical to the native serum matrix. To verify this, a variety of biochemical tests were performed on serum before and after the process of the present invention. (The "before" serum had been frozen twice, but not processed further.) The results of these comparisons are listed in Tables 1, 2 and 3. The serum chemistry profile was performed on a Hitachi 747 analyzer using routine chemistry methods developed by Boehringer Mannheim Co. The triglyceride assay was a glycerol-blanked peroxidase-linked enzymatic procedure. High density lipoprotein was separated from other lipids with magnesium phosphotungstate precipitation and the supernatant assayed for HDL cholesterol with a peroxidase-linked enzymatic reaction. Protein electrophoresis was performed with a commercial test system from Helena (cellulose acetate gel, barbital buffer, Ponceau S stain, and densitometer detection) (Helena Laboratories, Beaumont, Tex.). Lipoprotein electrophoresis was with the Corning Test System (universal gel and buffer, fat red stain) (Ciba Corning Diagnostics Corp., Palo Alto, Calif.).

To compare charcoal extraction of steroids, data from native serum carried through a typical charcoal treatment is included in Table 1. Serum (10 mLs) and activated charcoal (200 mg) were combined and mixed mechanically for two hours. The serum and charcoal were separated by centrifugation and filtration.

TABLE 1

| Analyte | Before Process | After Process Sorbent Extraction | After Process Charcoal Extraction |
|---|---|---|---|
| Sodium | 139.80 mmol/L | 137.70 | 142.50 |
| Potassium | 3.98 mmol/L | 3.84 | 4.82 |
| Chloride | 105.50 mmol/L | 104.60 | 107.50 |
| $CO_2$ | 21.50 mmol/L | 18.90 | 22.90 |
| Glucose | 86.00 mg/dL | 86.00 | 33.00 |
| BUN | 12.10 mg/dL | 12.20 | 10.50 |
| Creatinine | 0.86 mg/dL | 0.69 | 0.00 |
| Calcium | 9.25 mg/dL | 9.22 | 10.05 |
| Magnesium | 2.12 g/dL | 2.00 | 6.64 |
| Phosphorus | 3.45 mg/dL | 3.44 | 0.81 |
| Uric Acid | 4.46 mg/dL | 4.37 | 0.00 |
| Cholesterol | 172.00 mg/dL | 172.00 | 177.00 |
| Total Protein | 6.69 g/dL | 6.61 | 6.57 |
| Albumin | 4.27 g/dL | 4.26 | 4.09 |
| Bilirubin | 0.38 mg/dL | 0.19 | 0.04 |
| Enzymes: | | | |
| GGT | 17.0 U/L | 17.0 | 14.0 |
| Alk Phos | 74.0 U/L | 73.0 | 69.0 |
| AST | 31.0 U/L | 31.0 | 28.0 |
| LACDEH | 121.0 U/L | 119.0 | 90.0 |
| ALT | 32.0 U/L | 32.0 | 26.0 |

TABLE 2

| Analyte | Before Process | After Sorbent Process |
|---|---|---|
| Triglycerides | 134.0 mg/dL | 134.0 mg/dL |
| High Density Lipoprotein | 46.1 mg/dL | 46.5 mg/dL |

TABLE 3

| Protein Electrochoresis | | |
|---|---|---|
| Albumin | 4.05 g/dL | 4.05 g/dL |
| Globulins: | | |
| Alpha 1 | 0.15 g/dL | 0.15 g/dL |
| Alpha 2 | 1.10 g/dL | 1.08 g/dL |
| Beta | 0.91 g/dL | 0.85 g/dL |
| Gamma | 0.99 g/dL | 0.96 g/dL |

Lipoprotein electrophoresis demonstrated that migration patterns and intensity of stained bands were essentially identical for native serum samples and serum samples that have been processed with $C_{18}$ sorbent.

Note that charcoal-treated serum and sorbent-treated serum differ in several important ways. Most notably, the charcoal-treated serum had significant loss (overall range 24% to 100% decreased) of native glucose, creatinine, phosphorus, uric acid, bilirubin, and lactate dehydrogenase, as determined by the chemistry profile test. Charcoal also contaminated the serum and gave an increased (overall range 109% to 313% increase) potassium, calcium, and magnesium levels above that detected in the unprocessed serum.

The sorbent-processed serum was essentially identical to the unprocessed serum except bilirubin and creatinine were decreased 50% and 19%, respectively. Therefore, serum processed with sorbent was more like native serum than was serum treated with charcoal.

The steroid-free serum was tested for bacterial contamination. Samples were applied to various growth media (chocolate agar and thioglycollate broth, Remel, Lenexa, Kans.), incubated and evaluated. No bacterial growth was observed.

Table 4 summarizes results obtained when non-processed blood serum is analyzed by standard HPLC, RIA and GCMS methods. The HPLC determinations were by the following method (Lensmeyer, et al. *Clin. Chem.*, 34:471–474, 1984): Briefly, the drugs are isolated from serum with cyanopropyl-bounded silica (100 mg) and the resulting extract chromatographed on a Zorbax cyanopropyl HPLC analytical column to separate and quantitate the tricyclic drugs.

Each RIA was a separate kit and is referenced individually (See Table 4).

The GCMS (gas chromatography mass spectrometry) assays were performed by the following method: A serum sample was divided into two 1 mL portions. An acid (0.5N HCL) was added to one portion and a base (0.5N NaOH) was added to the other portion. Both samples were extracted with methylene chloride to recover drugs. The extracts were combined, concentrated and a portion injected onto a capillary DB 17 GC column (J&W Scientific, Folsom, Calif.) positioned in a GC-MS (Hewlett Packard, Rolling Meadows, Ill.) using a temperature programming 50° C. to 280° C. to elute the drugs.

TABLE 4

| Steroid | Normal Range | Lowest Detection Limit | Methodology |
|---|---|---|---|
| Cortisol | AM 60–240 ng/mL PM 30–120 ng/ml | 3 to 5 ng/mL | Extraction/HPLC |

TABLE 4-continued

| | | | |
|---|---|---|---|
| Cortisone | 5-25 ng/mL | 3 to 5 ng/mL | Extraction/HPLC |
| Corticosterone | 0 to 15 ng/mL | 3 to 5 ng/mL | Extraction/HPLC |
| Testosterone | .03-10 ng/mL | <0.1 ng/mL | RIA* |
| Androstenedione | 0-3.1 ng/mL | <0.1 ng/mL | RIA* |
| Progesterone | 0-400 ng/mL | >0.4 ng/mL | RIA* |
| 17-OH Progesterone | 0.2-3.04 ng/mL | >0.4 ng/mL | RIA* |
| DHEA Sulfate | 5-560 mcg/dL | >5 mcg/dL | RIA* |

| Drug | Therapeutic Range | Lowest Detection Limit | Methodology |
|---|---|---|---|
| Amitriptyline | 80-250 ng/mL | 8 to 10 ng/mL | Extraction/HPLC |
| Nortriptyline | 50-150 ng/mL | 8 to 10 ng/mL | Extraction/HPLC |
| Doxepin | 75-250 ng/mL | 8 to 10 ng/mL | Extraction/HPLC |
| Desdoxepin | 110-250 ng/mL | 8 to 10 ng/mL | Extraction/HPLC |
| Desipramin | 150-300 ng/mL | 8 to 10 ng/mL | Extraction/HPLC |
| Imipramine | 150-250 ng/mL | 8 to 10 ng/mL | Extraction/HPLC |
| Amoxepine | sum 200-500 ng/mL | 8 to 10 ng/mL | Extraction/HPLC |
| 8-OH Amoxepine | sum 200-500 ng/mL | 8 to 10 ng/mL | Extraction/HPLC |
| Caffeine | 2-10 mcg/mL | 0.05 to 0.1 mcg/mL | Extraction GCMS |
| Diazepam + Nordiazepam | 0.5-2.5 mcg/mL | 0.05 to 0.1 mcg/mL | Extraction GCMS |

*Testosterone: RIA, RSL I-125, double antibody. ICN Biomedicals, Inc., Costa Mesa, CA
Androstenedione: RIA, I-125, double antibody. Diagnostic Systems Laboratories, Inc., Webster, TX
Progesterone: RIA. Amerix-M I-125, single antibody. Eastman Kodak Company, Rochester, NY
17-OH Progesterone: RIA Coat-A-Count I-125, single antibody. Diagnostic Products Corporation, Los Angeles, CA
DHEA Sulfate: RIA, Coat-A-Count I-125, single antibody. Diagnostic Products Corporation, Los Angeles, CA Note that for those steroids measured by RIA, the detection limit is slightly greater than zero. However, the low end of the normal reference range for the respective steroid in blood is below the lower end of the detection limit. Clinically, this slight concentration difference is not significant and does not present a problem to the physician interpreting the test result. Accordingly, when a result is reported as less than the detection limit, the physician receives clinically useful information.

To quantitate the effectiveness of removing endogenous and exogenous steroids and exogenous drugs supplemented in native serum, assays were performed on serum before and after processing. These results are summarized in Table 5 below.

TABLE 5

| | Before Process | After Process |
|---|---|---|
| Steroid | | |
| Cortisol | 107.00 ng/mL | <5.0 ng/mL |
| Cortisone | 20.00 ng/mL | <5.0 ng/mL |
| Corticosterone | 4.00 ng/mL | <5.0 ng/mL |
| Testosterone | 1.50 ng/mL | <0.1 ng/mL |
| Androstenedione | 1.40 ng/mL | <0.1 ng/mL |
| Progesterone | 0.90 ng/mL | <0.4 ng/mL |
| 17-OH Progesterone | 0.65 ng/mL | <0.1 ng/mL |
| Dehydroepiandrosterone sulfate | 167.00 mcg/dL | <5.0 mcg/dL |
| Drug | | |
| Caffeine | 12.0 mcg/dL | <0.1 mcg/mL |
| Diazepam | 1.25 mcg/mL | <0.1 mcg/mL |
| Nordiazepam | 1.25 mcg/mL | <0.1 mcg/mL |
| Antidepressants: | | |
| Amitriptyline | 200 ng/mL | <10 ng/mL |
| Nortriptyline | 200 ng/mL | <10 ng/mL |
| Doxepin | 200 ng/mL | <10 ng/mL |
| Desdoxepin | 200 ng/mL | <10 ng/mL |
| Desipramin | 200 ng/mL | <10 ng/mL |
| Imipramine | 200 ng/mL | <10 ng/mL |
| Amoxepine | 200 ng/mL | <10 ng/mL |
| 8-OH Amoxepine | 200 ng/mL | <10 ng/mL |

The steroids and drugs that can be removed from serum are not limited just to those compounds described here. I envision that other steroid compounds and drugs are removed in the process.

Various modifications and alterations will be apparent to one skilled in the art without departing from the spirit and scope of the present invention. Only the claims are meant to limit the invention.

I claim:

1. A blood serum sample useful as a calibration baseline comprising a natural blood matrix, wherein said serum sample contains less than 5 ng/mL cortisol and wherein the sample is free of residual charcoal.

2. The serum sample of claim 1, additionally comprising less than 5 ng/mL cortisone, 5 ng/mL corticosterone, 0.4 ng/mL progesterone, 0.4 ng/mL 17-OH progesterone, 0.1 ng/mL androstenedione, 0.1 ng/mL testosterone, and 5 microgram/dL dehydroepiandrosterone sulfate.

3. The serum sample of claim 2, additionally comprising less than 10 ng/mL amitriptyline, nortriptyline, doxepin, desdoxepin, desipramin, imipramine, desipramine, amoxepine, 8-OH amoxepine.

4. The serum sample of claim 2, additionally comprising less than 0.1 microgram /mL each of caffeine, diazepam, and nordiazepam.

* * * * *

UNITED STATES PATENT AND TRADEMARK OFFICE
CERTIFICATE OF CORRECTION

PATENT NO.    : 5,308,768
DATED         : May 3, 1994
INVENTOR(S)   : Gary L. Lensmeyer It is certified that error appears in the above-identified patent and that said Letters Patent is hereby corrected as shown below:

| | |
|---|---|
| Column 2, line 53 | "mass    spectrometry" s/b "mass spectrometry" |
| Column 3, line 11 | "crticosterone" s/b "corticosterone" |
| Column 4, line 4 | "he" s/b "the" |
| Column 6, lines 20 and 21 | "1. Preparation Of Serum With Reduced Levels Of Steroids And Drugs" s/b "PREPARATION OF SERUM WITH REDUCED LEVELS OF STEROIDS AND DRUGS" |
| Column 8, line 2 | "Electrochoresis" s/b "Electrophoresis" |
| Column 9, line 6 | ">0.4 ng/mL" s/b "<0.4 ng/mL" |
| Column 9, line 7 | ">0.4 ng/mL" s/b "<0.4 ng/mL" |
| Column 9, line 8 | ">5 mcg/dL" s/b "<5 mcg/dL" |

Signed and Sealed this

Sixteenth Day of August, 1994

BRUCE LEHMAN

Attest:

*Attesting Officer*    *Commissioner of Patents and Trademarks*